(12) United States Patent
Leven

(10) Patent No.: US 10,071,242 B2
(45) Date of Patent: Sep. 11, 2018

(54) LEAD ANCHOR FOR AN ELECTRICAL STIMULATION SYSTEM

(71) Applicant: Boston Scientific Neuromodulation Corporation, Valencia, CA (US)

(72) Inventor: Jacob B. Leven, Huntington Beach, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 58 days.

(21) Appl. No.: 15/442,414

(22) Filed: Feb. 24, 2017

(65) Prior Publication Data

US 2017/0246454 A1     Aug. 31, 2017

Related U.S. Application Data

(60) Provisional application No. 62/301,496, filed on Feb. 29, 2016.

(51) Int. Cl.
*A61N 1/05* (2006.01)
*A61N 1/36* (2006.01)

(52) U.S. Cl.
CPC ......... *A61N 1/0558* (2013.01); *A61N 1/0539* (2013.01); *A61N 1/3605* (2013.01)

(58) Field of Classification Search
None
See application file for complete search history.

(56) References Cited

U.S. PATENT DOCUMENTS

| | | |
|---|---|---|
| 376,810 A | 1/1888 | Brill |
| 612,685 A | 10/1898 | Thorp et al. |
| 2,046,837 A | 7/1936 | Phillips |
| 3,866,615 A | 2/1975 | Hewson |
| 4,141,752 A | 2/1979 | Shipko |

(Continued)

FOREIGN PATENT DOCUMENTS

| | | |
|---|---|---|
| EP | 85417 A1 | 8/1983 |
| EP | 0597213 A1 | 5/1994 |

(Continued)

OTHER PUBLICATIONS

U.S. Appl. No. 15/156,193, filed May 16, 2016.

(Continued)

*Primary Examiner* — Ankit D Tejani
(74) *Attorney, Agent, or Firm* — Lowe Graham Jones PLLC; Bruce E. Black

(57) ABSTRACT

A lead anchor includes an anchor body having a band section, guide members and a support section. The guide members and the support section are spaced apart from each other and define a band channel. Further, the lead anchor includes a flexible band that is coupleable to the guide members with at least a portion of the flexible band positionable within the band channel. The flexible band and the support section define a first lead channel having a spaced-apart distance between the flexible band and the support section. The first lead channel includes an open side for allowing a lateral ingress or egress of a portion of a lead. The lead anchor further includes a fastener movable relative to the anchor body to reduce or increase the spaced-apart distance of the first lead channel to hold or release, respectively, the portion of the lead within the first lead channel.

20 Claims, 15 Drawing Sheets

(56) References Cited

U.S. PATENT DOCUMENTS

| | | | |
|---|---|---|---|
| 4,276,882 A | 7/1981 | Dickhudt et al. |
| 4,316,471 A | 2/1982 | Shipko et al. |
| 4,462,401 A | 7/1984 | Burgio |
| 4,632,670 A | 12/1986 | Mueller, Jr. |
| 4,764,132 A | 8/1988 | Stutz, Jr. |
| 4,858,623 A | 8/1989 | Bradshaw et al. |
| 5,036,862 A | 8/1991 | Pohndorf |
| 5,107,856 A | 4/1992 | Kristiansen et al. |
| 5,158,097 A | 10/1992 | Christlieb |
| 5,228,248 A | 7/1993 | Haddock |
| 5,269,809 A | 12/1993 | Hayhurst et al. |
| 5,370,662 A | 12/1994 | Stone et al. |
| 5,376,108 A | 12/1994 | Collins et al. |
| 5,484,445 A | 1/1996 | Knuth |
| 5,584,874 A | 12/1996 | Rugland et al. |
| 5,628,780 A | 5/1997 | Helland et al. |
| 5,746,722 A | 5/1998 | Pohndorf et al. |
| 5,865,843 A | 2/1999 | Baudino |
| 5,895,360 A | 4/1999 | Christopherson et al. |
| 5,957,968 A | 9/1999 | Belden et al. |
| 6,175,710 B1 | 1/2001 | Kamaji et al. |
| 6,181,969 B1 | 1/2001 | Gord |
| 6,192,279 B1 | 2/2001 | Barreras, Sr. et al. |
| 6,224,450 B1 | 5/2001 | Norton |
| 6,271,094 B1 | 8/2001 | Boyd et al. |
| 6,295,944 B1 | 10/2001 | Lovett |
| 6,360,750 B1 | 3/2002 | Gerber et al. |
| 6,364,278 B1 | 4/2002 | Lin et al. |
| 6,391,985 B1 | 5/2002 | Goode et al. |
| 6,473,654 B1 | 10/2002 | Chinn |
| 6,516,227 B1 | 2/2003 | Meadows et al. |
| 6,606,523 B1 | 8/2003 | Jenkins |
| 6,609,029 B1 | 8/2003 | Mann et al. |
| 6,609,032 B1 | 8/2003 | Woods et al. |
| 6,741,892 B1 | 5/2004 | Meadows et al. |
| 6,792,314 B2 | 9/2004 | Byers et al. |
| 6,847,849 B2 | 1/2005 | Mamo et al. |
| 6,901,287 B2 | 5/2005 | Davis et al. |
| 6,978,180 B2 | 12/2005 | Tadlock |
| 6,984,145 B1 | 1/2006 | Lim |
| 7,069,083 B2 | 6/2006 | Finch et al. |
| 7,072,719 B2 | 7/2006 | Vinup et al. |
| 7,161,461 B1 | 1/2007 | Nelson |
| 7,184,841 B1 | 2/2007 | Bodner et al. |
| 7,203,548 B2 | 4/2007 | Whitehurst et al. |
| 7,235,078 B2 | 7/2007 | West, Jr. |
| 7,244,150 B1 | 7/2007 | Brase et al. |
| 7,343,202 B2 | 3/2008 | Mrva et al. |
| 7,402,076 B1 | 7/2008 | Lim |
| 7,437,193 B2 | 10/2008 | Parramon et al. |
| 7,447,546 B2 | 11/2008 | Kim et al. |
| 7,450,997 B1 | 11/2008 | Pianca et al. |
| 7,596,414 B2 | 9/2009 | Whitehurst et al. |
| 7,610,102 B2 | 10/2009 | Kowalczyk |
| 7,610,103 B2 | 10/2009 | Whitehurst et al. |
| 7,672,734 B2 | 3/2010 | Anderson et al. |
| 7,761,165 B1 | 7/2010 | He et al. |
| 7,783,359 B2 | 8/2010 | Meadows |
| 7,787,960 B2 | 8/2010 | Lubenow |
| 7,792,590 B1 | 9/2010 | Pianca et al. |
| 7,809,446 B2 | 10/2010 | Meadows |
| 7,848,803 B1 | 12/2010 | Jaax et al. |
| 7,853,321 B2 | 12/2010 | Jaax et al. |
| 7,860,568 B2 | 12/2010 | Deininger et al. |
| 7,949,395 B2 | 5/2011 | Kuzma |
| 7,974,706 B2 | 7/2011 | Moffitt et al. |
| 8,175,710 B2 | 5/2012 | He |
| 8,224,450 B2 | 7/2012 | Brase |
| 8,224,451 B2 | 7/2012 | Jaax et al. |
| 8,229,573 B2 | 7/2012 | Chen et al. |
| 8,315,704 B2 | 11/2012 | Jaax et al. |
| 8,364,278 B2 | 1/2013 | Pianca et al. |
| 8,568,462 B2 | 10/2013 | Sixto et al. |
| 8,676,341 B2 * | 3/2014 | Kane ............... A61B 17/0401 607/116 |
| 8,688,232 B2 | 4/2014 | Finley et al. |
| 2001/0000187 A1 | 4/2001 | Peckham et al. |
| 2002/0107554 A1 | 8/2002 | Biggs et al. |
| 2003/0074023 A1 | 4/2003 | Kaplan et al. |
| 2003/0078623 A1 | 4/2003 | Weinberg et al. |
| 2003/0208247 A1 | 11/2003 | Spinelli et al. |
| 2004/0059392 A1 | 3/2004 | Parramon et al. |
| 2005/0033393 A1 | 2/2005 | Daglow |
| 2005/0165465 A1 | 7/2005 | Pianca et al. |
| 2005/0283202 A1 | 12/2005 | Gellman |
| 2005/0288760 A1 | 12/2005 | Machado et al. |
| 2006/0127158 A1 | 6/2006 | Olson et al. |
| 2006/0161235 A1 | 7/2006 | King |
| 2006/0173520 A1 | 8/2006 | Olson |
| 2006/0205995 A1 | 9/2006 | Browning |
| 2006/0206162 A1 | 9/2006 | Wahlstrand et al. |
| 2007/0010794 A1 | 1/2007 | Dann et al. |
| 2007/0050005 A1 | 3/2007 | Lauro |
| 2007/0078399 A1 | 4/2007 | Olson |
| 2007/0100348 A1 | 5/2007 | Cauthen et al. |
| 2007/0150036 A1 | 6/2007 | Anderson |
| 2007/0219595 A1 | 9/2007 | He |
| 2007/0255369 A1 | 11/2007 | Bonde et al. |
| 2008/0071320 A1 | 3/2008 | Brase |
| 2008/0091255 A1 | 4/2008 | Caparso et al. |
| 2008/0140130 A1 | 6/2008 | Chan et al. |
| 2008/0140169 A1 | 6/2008 | Imran |
| 2008/0172116 A1 | 7/2008 | Mrva et al. |
| 2008/0183241 A1 | 7/2008 | Bedenbaugh |
| 2008/0183253 A1 | 7/2008 | Bly |
| 2008/0196939 A1 | 8/2008 | Lubenow et al. |
| 2008/0228251 A1 | 9/2008 | Hill |
| 2008/0243220 A1 | 10/2008 | Barker |
| 2008/0275401 A1 * | 11/2008 | Sage ............... A61M 25/02 604/175 |
| 2008/0312712 A1 | 12/2008 | Penner |
| 2009/0018601 A1 | 1/2009 | Deininger et al. |
| 2009/0112272 A1 | 4/2009 | Schleicher et al. |
| 2009/0187222 A1 | 7/2009 | Barker |
| 2009/0198312 A1 | 8/2009 | Barker |
| 2009/0210043 A1 | 8/2009 | Reddy |
| 2009/0254151 A1 | 10/2009 | Anderson et al. |
| 2009/0259260 A1 | 10/2009 | Bentley et al. |
| 2009/0270940 A1 | 10/2009 | Deininger |
| 2009/0276021 A1 | 11/2009 | Meadows et al. |
| 2009/0281571 A1 | 11/2009 | Weaver et al. |
| 2009/0281576 A1 | 11/2009 | Weaver et al. |
| 2009/0281579 A1 | 11/2009 | Weaver et al. |
| 2010/0076535 A1 | 3/2010 | Pianca et al. |
| 2010/0094425 A1 | 4/2010 | Bentley et al. |
| 2010/0174240 A1 | 7/2010 | Wells et al. |
| 2010/0268298 A1 | 10/2010 | Moffitt et al. |
| 2010/0274336 A1 | 10/2010 | Nguyen-stella et al. |
| 2010/0286670 A1 | 11/2010 | Doyle et al. |
| 2010/0312319 A1 | 12/2010 | Barker |
| 2011/0004267 A1 | 1/2011 | Meadows |
| 2011/0022066 A1 | 1/2011 | Sevrain |
| 2011/0022142 A1 | 1/2011 | Barker et al. |
| 2011/0060395 A1 | 3/2011 | Cantlon |
| 2011/0078900 A1 | 4/2011 | Pianca et al. |
| 2011/0130817 A1 | 6/2011 | Chen |
| 2011/0130818 A1 | 6/2011 | Chen |
| 2011/0178573 A1 | 7/2011 | Nguyen-stella et al. |
| 2011/0238129 A1 | 9/2011 | Moffitt et al. |
| 2011/0264180 A1 | 10/2011 | Hamilton |
| 2011/0313500 A1 | 12/2011 | Barker et al. |
| 2012/0016378 A1 | 1/2012 | Pianca et al. |
| 2012/0046710 A1 | 2/2012 | Digiore et al. |
| 2012/0071949 A1 | 3/2012 | Pianca et al. |
| 2012/0150202 A1 | 6/2012 | Chen et al. |
| 2012/0165911 A1 | 6/2012 | Pianca |
| 2012/0185027 A1 | 7/2012 | Pianca et al. |
| 2012/0197375 A1 | 8/2012 | Pianca et al. |
| 2012/0203316 A1 | 8/2012 | Moffitt et al. |
| 2012/0203320 A1 | 8/2012 | DiGiore et al. |
| 2012/0203321 A1 | 8/2012 | Moffitt et al. |
| 2012/0232626 A1 | 9/2012 | Daglow |
| 2012/0277670 A1 | 11/2012 | Goetz |
| 2012/0283835 A1 | 11/2012 | Bentley et al. |

(56) References Cited

U.S. PATENT DOCUMENTS

| | | |
|---|---|---|
| 2012/0316615 A1 | 12/2012 | Digiore et al. |
| 2012/0330355 A1 | 12/2012 | Finley et al. |
| 2013/0096659 A1 | 4/2013 | Ranu |
| 2013/0105071 A1 | 5/2013 | Digiore et al. |
| 2013/0149031 A1 | 6/2013 | Changsrivong |
| 2013/0204336 A1 | 8/2013 | Sharma |
| 2013/0238023 A1 | 9/2013 | Wales et al. |
| 2014/0074093 A9 | 3/2014 | Nelson et al. |
| 2014/0180345 A1 | 6/2014 | Chan et al. |
| 2014/0343645 A1 | 11/2014 | Wechter |
| 2015/0005856 A1 | 1/2015 | Pianca et al. |
| 2015/0018916 A1* | 1/2015 | Leven ............... A61N 1/0553 607/116 |
| 2015/0045865 A1 | 2/2015 | Nageri et al. |
| 2015/0051674 A1 | 2/2015 | Barner et al. |
| 2015/0051675 A1 | 2/2015 | Barner |
| 2015/0066121 A1 | 3/2015 | Govea et al. |
| 2015/0246216 A1 | 9/2015 | Barker |

FOREIGN PATENT DOCUMENTS

| | | |
|---|---|---|
| JP | H07-014681 | 3/1995 |
| JP | 2001339829 A | 12/2001 |
| WO | 1998033551 A1 | 8/1998 |
| WO | 1999/053994 | 10/1999 |
| WO | 2000/013743 A2 | 3/2000 |
| WO | 2000/064535 | 11/2000 |
| WO | 2004/054655 | 7/2004 |
| WO | 2006/086363 A2 | 8/2006 |
| WO | 2007/056384 A2 | 5/2007 |
| WO | 2007/083108 A2 | 7/2007 |
| WO | 2007/149994 A2 | 12/2007 |
| WO | 2008/094789 A1 | 8/2008 |
| WO | 2008101026 A1 | 8/2008 |
| WO | 2008/121708 A2 | 10/2008 |
| WO | 2010/126853 A1 | 11/2010 |
| WO | 2012151356 A1 | 11/2012 |
| WO | 2013112920 A1 | 8/2013 |

OTHER PUBLICATIONS

U.S. Appl. No. 14/312,194, filed Jun. 23, 2014.
U.S. Appl. No. 14/457,602, filed Aug. 12, 2014.
U.S. Appl. No. 14/457,640, filed Aug. 2, 2014.
U.S. Appl. No. 14/452,467, filed Aug. 5, 2014.
U.S. Appl. No. 14/630,124, filed Feb. 24, 205.
U.S. Appl. No. 14/720,708, filed May 22, 2015.
U.S. Appl. No. 15/225,664, filed Aug. 1, 2016.
U.S. Appl. No. 62/301,496, filed Feb. 29, 2016.
U.S. Appl. No. 12/177,823, filed Jul. 22, 2008.
U.S. Appl. No. 13/750,725, filed Jan. 25, 2013.
International Search Report and Written Opinion from International Patent Application No. PCT/US2017/019499, dated Apr. 24, 2017.
U.S. Appl. No. 15/156,193, Entitled: Torque Lock Anchor and Methods and Devices Using the Anchor, Inventor: Nguyen-Stella et al., filed May 16, 2016, 40 pages.
U.S. Appl. No. 14/312,194, Entitled: Lead Anchors and Systems and Methods Using the Lead Anchors, Inventor: Pianca et al., filed Jun. 23, 2014, 35 pages.
U.S. Appl. No. 14/457,602, Entitled: Lead Anchors and Systems and Methods Employing the Lead Anchors, Inventor: Barner et al., filed Aug. 12, 2014, 37 pages.
U.S. Appl. No. 14/457,640, Entitled: Lead Anchor with Adhesive and Systems and Methods Using the Lead Anchor, Inventor: Paul Keith Barner, filed Aug. 12, 2014, 34 pages.
U.S. Appl. No. 14/452,467, Entitled: Systems and Methods for Making and Using Lead Anchors for Leads of Electrical Stimulation Systems, Inventor: Nageri et al., filed Aug. 5, 2014, 41 pages.
U.S. Appl. No. 14/630,124, Entitled: Side Loading Lead Anchor and Methods of Making and Using Thereof, Inventor: John Michael Barker, filed Feb. 24, 2015, 32 pages.
U.S. Appl. No. 14/720,708, Entitled: Systems and Methods for Making and Using Reversible Mechanical Lead Anchors for Electrical Stimulation Systems, Inventor: Nageri et al., filed May 22, 2015, 34 pages.
U.S. Appl. No. 15/225,664, Entitled: Lead Anchor with a Wedge and Systems Using the Lead Anchor, Inventor: Jacob B. Leven, filed Aug. 1, 2016, 37 pages.
U.S. Appl. No. 62/301,496, Entitled: Lead Anchor for an Electrical Stimulation System, Inventor: Jacob B. Leven, filed Feb. 29, 2016, 40 pages.
U.S. Appl. No. 12/177,823, Entitled: Lead with Transition and Methods of Manufacture and Use, Inventor: Pianca et al., filed Jul. 22, 2008, 22 pages.
U.S. Appl. No. 13/750,725, Entitled: Systems and Methods for Identifying the Circumferential Positioning of Electrodes of Leads for Electrical Stimulation Systems, Inventor: Pianca et al., filed Jan. 25, 2013, 36 pages.

* cited by examiner

LEAD ANCHOR FOR AN ELECTRICAL STIMULATION SYSTEM

CROSS-REFERENCE TO RELATED APPLICATIONS

This application claims the benefit under 35 U.S.C. § 119(e) of U.S. Provisional Patent Application Ser. No. 62/301,496, filed Feb. 29, 2016, which is incorporated herein by reference.

FIELD

The present invention is directed to the area of implantable electrical stimulation systems and methods of making and implanting the same. More specifically, the present invention is directed to a side loading lead anchor for an electrical stimulation system.

BACKGROUND

Implantable electrical stimulation systems have proven therapeutic in a variety of diseases and disorders. For example, spinal cord stimulation systems have been used as a therapeutic modality for the treatment of chronic pain syndromes. Peripheral nerve stimulation has been used to treat chronic pain syndrome and incontinence, with a number of other applications under investigation. Functional electrical stimulation systems have been applied to restore some functionality to paralyzed extremities in spinal cord injury patients. Stimulation of the brain, such as deep brain stimulation, can be used to treat a variety of diseases or disorders.

Stimulators have been developed to provide therapy for a variety of treatments. A stimulator can include a control module (with a pulse generator), one or more leads, and an array of stimulator electrodes on each lead. The stimulator electrodes are in contact with or near the nerves, muscles, or other tissue to be stimulated. The pulse generator in the control module generates electrical pulses that are delivered by the electrodes to body tissue.

BRIEF SUMMARY

In at least some embodiments, a lead anchor includes an anchor body having a band section, guide members and a support section. The guide members and the support section are spaced apart from each other in a fixed relationship. The band section and guide members define a band channel. Further, the lead anchor includes a flexible band that is coupleable to the guide members. At least a portion of the flexible band is positionable within the band channel. The flexible band and the support section define a first lead channel comprising a spaced-apart distance between the flexible band and the support section. The first lead channel includes an open side for allowing a lateral ingress or egress of a portion of a lead. The lead anchor further includes a fastener selectively movable relative to the anchor body to reduce or increase the spaced-apart distance of the first lead channel to hold or release, respectively, the portion of the lead within the first lead channel.

In at least some embodiments, the guide members are integrally formed with the anchor body. In at least some embodiments, the flexible band forms a continuous loop in which opposite ends of the loop are disposed around the guide members. Alternatively, the lead anchor includes a flexible band having bulbous end portions that are larger than an opening of the band channel.

In at least some embodiments, the fastener is a set screw. The fastener may directly engage with the flexible band.

In at least some embodiments, the anchor body includes a rigid wall extending between the band section and the support section to maintain the band section in the fixed relationship with the support section.

In at least some embodiments, reducing the spaced-apart distance of the first lead channel places the lead channel in a closed position and increasing the spaced-apart distance of the first lead channel places the lead channel in an open position.

In at least some embodiments, the lead anchor includes an exterior body encapsulating at least a portion of the anchor body and a thickness of the exterior body varies along a longitudinal direction of the exterior body. The exterior body may include an end portion or portions. In at least some embodiments, at least one end portion defines a second lead channel having an open side to laterally receive another portion of the lead. In at least some embodiments, the second lead channel includes a retention region that is larger than an inlet region.

Another embodiment is an electrical stimulation system that includes the lead anchor described above, a control module having a housing, an electronic subassembly disposed in the housing, and a lead having an array of electrodes selectively controllable by the control module. A lead body carries a plurality of conductors that are electrically coupled to the control module and electrically coupled to the array of electrodes, in which a portion of the lead body is laterally insertable into or extractable from the first lead channel of the lead anchor.

In at least some embodiments, the electrical stimulation system includes an exterior body encapsulating at least a portion of the anchor body. The exterior body includes an end portion or end portions. In at least some embodiments, at least one of the end portions defines a second lead channel having an open side to laterally receive another portion of the lead body. In at least some embodiments, the second lead channel includes a retention region that is larger than an inlet region.

In at least some embodiments, a method of assembling a lead with a lead anchor, as described above, includes the steps of (1) laterally inserting an intermediate portion of the lead through an open side of a first lead channel of the lead anchor; and (2) reducing a spaced-apart distance of the first lead channel to capture the intermediate portion of the lead within the lead anchor.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of implantable electrical stimulation systems and methods of making and using the systems. The present invention is also directed to implantable electrical stimulation cuff devices, as well as methods of making and using the same.

Suitable implantable electrical stimulation systems include, but are not limited to, a least one lead with one or more electrodes disposed along a distal end of the lead. Leads include, for example, percutaneous leads, paddle leads, and cuff leads. Examples of electrical stimulation systems with leads are found in, for example, U.S. Pat. Nos. 6,181,969; 6,516,227; 6,609,029; 6,609,032; 6,741,892; 7,203,548; 7,244,150; 7,450,997; 7,596,414; 7,610,103; 7,672,734; 7,761,165; 7,783,359; 7,792,590; 7,809,446; 7,949,395; 7,974,706; 6,175,710; 6,224,450; 6,271,094; 6,295,944; 6,364,278; and 6,391,985; U.S. Patent Applications Publication Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; and 2013/0105071; and U.S. patent application Ser. Nos. 12/177,823 and 13/750,725, all of which are incorporated by reference in their entireties. An example of a lead anchor may be found in U.S. Patent Publication No. 2012/0185027, which is incorporated by reference in its entirety.

Figure 1:
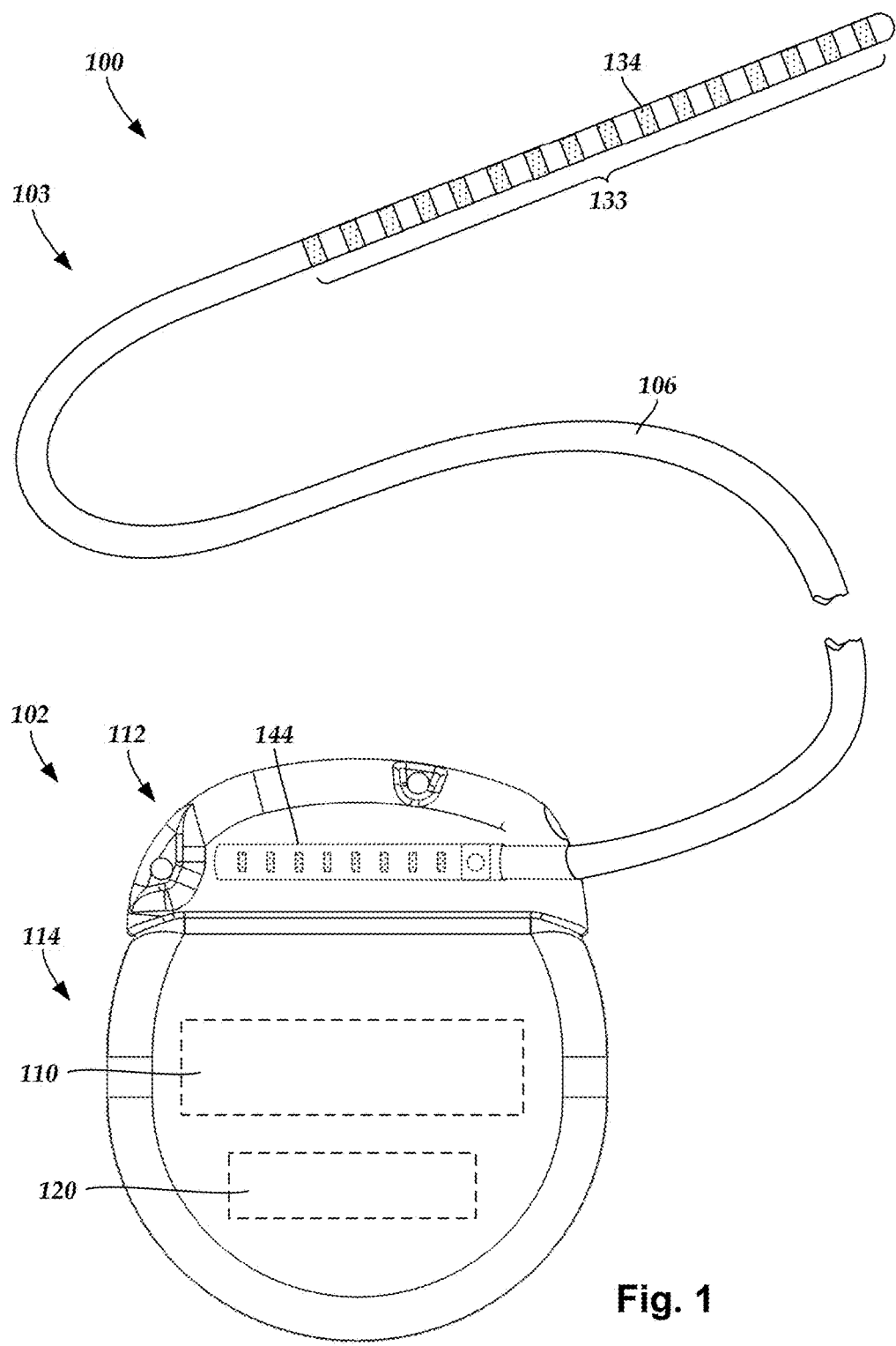
FIG. 1 is a schematic view of one embodiment of an electrical stimulation system that includes a lead electrically coupled to a control module according to an embodiment of the present invention.

FIG. 1 illustrates schematically one embodiment of an electrical stimulation system 100. The electrical stimulation system includes a control module (e.g., a stimulator or pulse generator) 102 and a lead 103 coupleable to the control module 102. The lead 103 includes one or more lead bodies 106, an array of electrodes 133, such as electrode 134, and an array of terminals (e.g., 210 in FIG. 2A-2B) disposed along the one or more lead bodies 106. In at least some embodiments, the lead is isodiametric along a longitudinal length of the lead body 106.

The lead 103 can be coupled to the control module 102 in any suitable manner. In at least some embodiments, the lead 103 couples directly to the control module 102. In at least some other embodiments, the lead 103 couples to the control module 102 via one or more intermediate devices (200 in FIGS. 2A-2B). For example, in at least some embodiments one or more lead extensions 224 (see e.g., FIG. 2B) can be disposed between the lead 103 and the control module 102 to extend the distance between the lead 103 and the control module 102. Other intermediate devices may be used in addition to, or in lieu of, one or more lead extensions including, for example, a splitter, an adaptor, or the like or combinations thereof. It will be understood that, in the case where the electrical stimulation system 100 includes multiple elongated devices disposed between the lead 103 and the control module 102, the intermediate devices may be configured into any suitable arrangement.

The control module 102 typically includes a connector housing 112 and a sealed electronics housing 114. Stimulation circuitry 110 and an optional power source 120 are disposed in the electronics housing 114. A control module connector 144 is disposed in the connector housing 112. The control module connector 144 is configured and arranged to make an electrical connection between the lead 103 and the stimulation circuitry 110 of the control module 102.

The electrical stimulation system or components of the electrical stimulation system, including the lead body 106 and the control module 102, are typically implanted into the body of a patient. The electrical stimulation system can be used for a variety of applications including, but not limited to, brain stimulation, neural stimulation, spinal cord stimulation, muscle stimulation, and the like.

The electrodes 134 can be formed using any conductive, biocompatible material. Examples of suitable materials include metals, alloys, conductive polymers, conductive carbon, and the like, as well as combinations thereof. In at least some embodiments, one or more of the electrodes 134 are formed from one or more of: platinum, platinum iridium, palladium, palladium rhodium, or titanium. The number of electrodes 134 in each array 133 may vary. For example, there can be two, four, six, eight, ten, twelve, fourteen, sixteen, or more electrodes 134. As will be recognized, other numbers of electrodes 134 may also be used.

The electrodes of the lead body 106 are typically disposed in, or separated by, a non-conductive, biocompatible material such as, for example, silicone, polyurethane, polyetheretherketone ("PEEK"), epoxy, and the like or combinations thereof. The lead body 106 may be formed in the desired shape by any process including, for example, molding (including injection molding), casting, and the like. The non-conductive material typically extends from the distal end of the lead body 106 to the proximal end of the lead body 106.

Figure 2A:
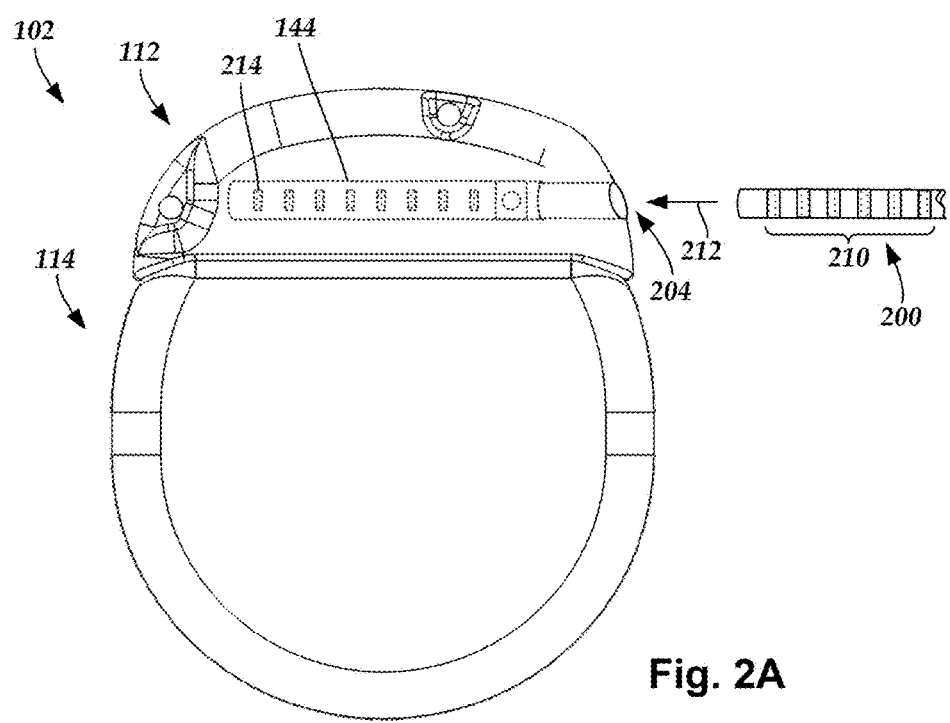
FIG. 2A is a schematic view of one embodiment of the control module of FIG. 1 configured and arranged to electrically couple to an elongated device according to an embodiment of the present invention.
Figure 2B:
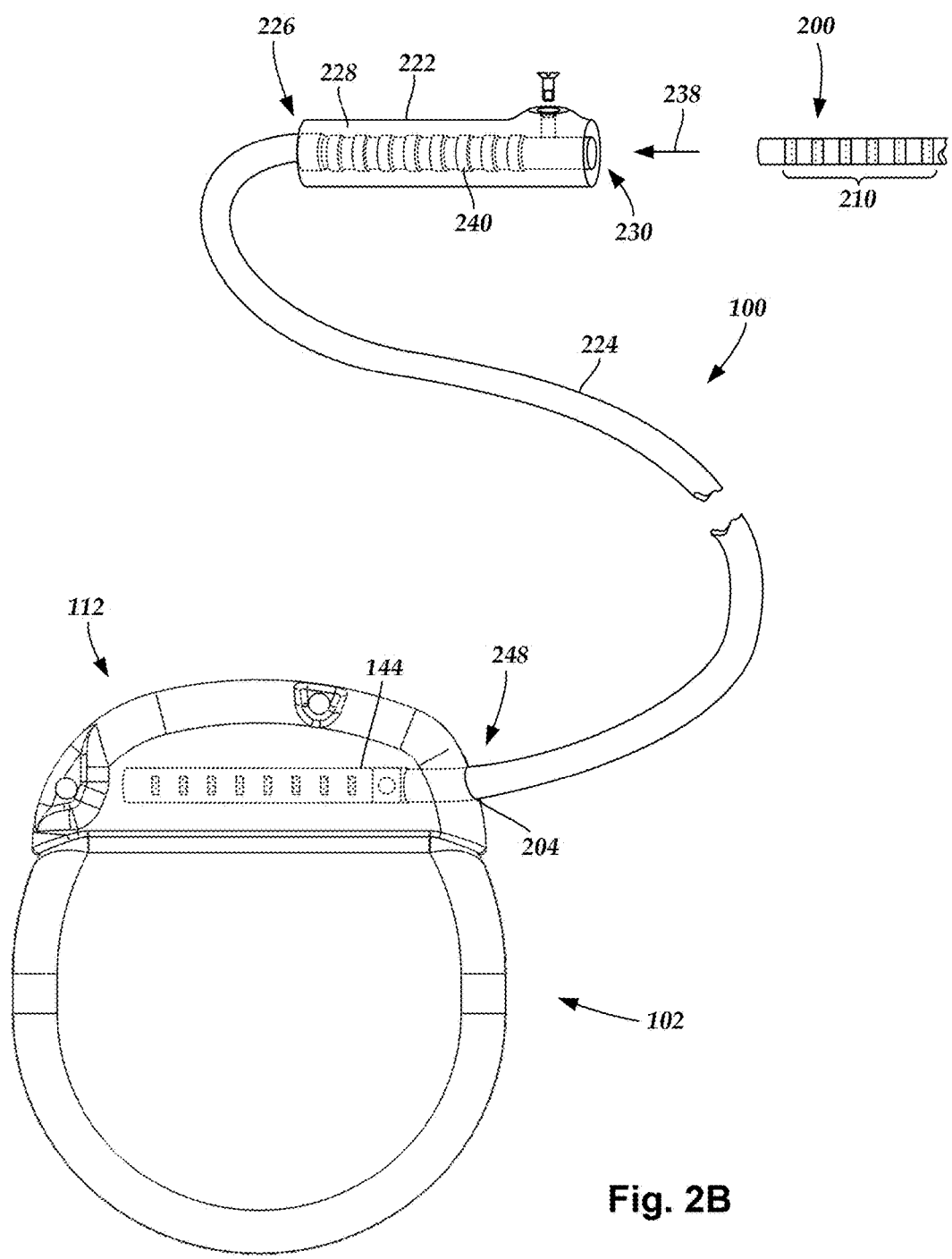
FIG. 2B is a schematic view of one embodiment of a lead extension configured and arranged to electrically couple the elongated device of FIG. 2A to the control module of FIG. 1 according to an embodiment of the present invention.

Terminals (e.g., 210 in FIGS. 2A-2B) are typically disposed along the proximal end of the lead body 106 of the electrical stimulation system 100 (as well as any splitters, lead extensions, adaptors, or the like) for electrical connection to corresponding connector contacts (e.g., 214 and 240 in FIG. 2B). The connector contacts are disposed in connectors (e.g., 144 in FIGS. 1-2B; and 222 in FIG. 2B) which, in turn, are disposed on, for example, the control module 102 (or a lead extension, a splitter, an adaptor, or the like). Electrically conductive wires, cables, or the like (not shown) extend from the terminals to the electrodes 134. Typically, one or more electrodes 134 are electrically coupled to each terminal. In at least some embodiments, each terminal is only connected to one electrode 134.

The electrically conductive wires ("conductors") may be embedded in the non-conductive material of the lead body 106 or can be disposed in one or more lumens (not shown) extending along the lead body 106. In some embodiments, there is an individual lumen for each conductor. In other embodiments, two or more conductors extend through a lumen. There may also be one or more lumens (not shown) that open at, or near, the proximal end of the lead body 106, for example, for inserting a stylet to facilitate placement of the lead body 106 within a body of a patient. Additionally, there may be one or more lumens (not shown) that open at, or near, the distal end of the lead body 106, for example, for infusion of drugs or medication into the site of implantation of the lead body 106. In at least one embodiment, the one or more lumens are flushed continually, or on a regular basis, with saline, epidural fluid, or the like. In at least some embodiments, the one or more lumens are permanently or removably sealable at the distal end.

FIG. 2A is a schematic side view of one embodiment of a proximal end of one or more elongated devices 200 configured and arranged for coupling to one embodiment of the control module connector 144. The one or more elongated devices may include, for example, the lead body 106, one or more intermediate devices (e.g., the lead extension 224 of FIG. 2B, an adaptor, or the like or combinations thereof), or a combination thereof.

The control module connector 144 defines at least one port into which a proximal end of the elongated device 200 can be inserted, as shown by directional arrow 212. In FIG. 2A (and in other figures), the connector housing 112 is shown having one port 204. The connector housing 112 can define any suitable number of ports including, for example, one, two, three, four, five, six, seven, eight, or more ports.

The control module connector 144 also includes a plurality of connector contacts, such as connector contact 214, disposed within each port 204. When the elongated device 200 is inserted into the port 204, the connector contacts 214 can be aligned with a plurality of terminals 210 disposed along the proximal end(s) of the elongated device(s) 200 to electrically couple the control module 102 to the electrodes (134 of FIG. 1) disposed at a distal end of the lead 103. Examples of connectors in control modules are found in, for example, U.S. Pat. Nos. 7,244,150 and 8,224,450, which are incorporated by reference.

FIG. 2B is a schematic side view of another embodiment of the electrical stimulation system 100. The electrical stimulation system 100 includes a lead extension 224 that is configured and arranged to couple one or more elongated devices 200 (e.g., the lead body 106, an adaptor, another lead extension, or the like or combinations thereof) to the control module 102. In FIG. 2B, the lead extension 224 is shown coupled to a single port 204 defined in the control module connector 144. Additionally, the lead extension 224 is shown configured and arranged to couple to a single elongated device 200. In alternate embodiments, the lead extension 224 is configured and arranged to couple to multiple ports 204 defined in the control module connector 144, or to receive multiple elongated devices 200, or both.

A lead extension connector 222 is disposed on the lead extension 224. In FIG. 2B, the lead extension connector 222 is shown disposed at a distal end 226 of the lead extension 224. The lead extension connector 222 includes a connector housing 228. The connector housing 228 defines at least one port 230 into which terminals 210 of the elongated device 200 can be inserted, as shown by directional arrow 238. The connector housing 228 also includes a plurality of connector contacts, such as connector contact 240. When the elongated device 200 is inserted into the port 230, the connector contacts 240 disposed in the connector housing 228 can be aligned with the terminals 210 of the elongated device 200 to electrically couple the lead extension 224 to the electrodes (134 of FIG. 1) disposed along the lead (103 in FIG. 1).

In at least some embodiments, the proximal end of the lead extension 224 is similarly configured and arranged as a proximal end of the lead 103 (or other elongated device 200). The lead extension 224 may include a plurality of electrically conductive wires (not shown) that electrically couple the connector contacts 240 to a proximal end 248 of the lead extension 224 that is opposite to the distal end 226. In at least some embodiments, the conductive wires disposed in the lead extension 224 can be electrically coupled to a plurality of terminals (not shown) disposed along the proximal end 248 of the lead extension 224. In at least some embodiments, the proximal end 248 of the lead extension 224 is configured and arranged for insertion into a connector disposed in another lead extension (or another intermediate device). In other embodiments (and as shown in FIG. 2B), the proximal end 248 of the lead extension 224 is configured and arranged for insertion into the control module connector 144.

Lead anchors, which are often used on leads of electrical stimulation systems, are typically used to prevent the migration of neuromodulation leads. The lead anchor is attached to a lead body and also attached to patient tissue to reduce or minimize post-implantation lead migration. Some conventional lead anchors are placed onto the lead body by sliding one end of the lead body through a circumscribed passage in the lead anchor.

In at least some embodiments of the present invention, the lead anchor can side load an intermediate portion of the lead body at any suitable position along the lead body. The lead anchor is particularly useful with loads having proximal or distal array lead designs that may have a wider diameter than the intermediate portion of the lead body.

Figure 3:
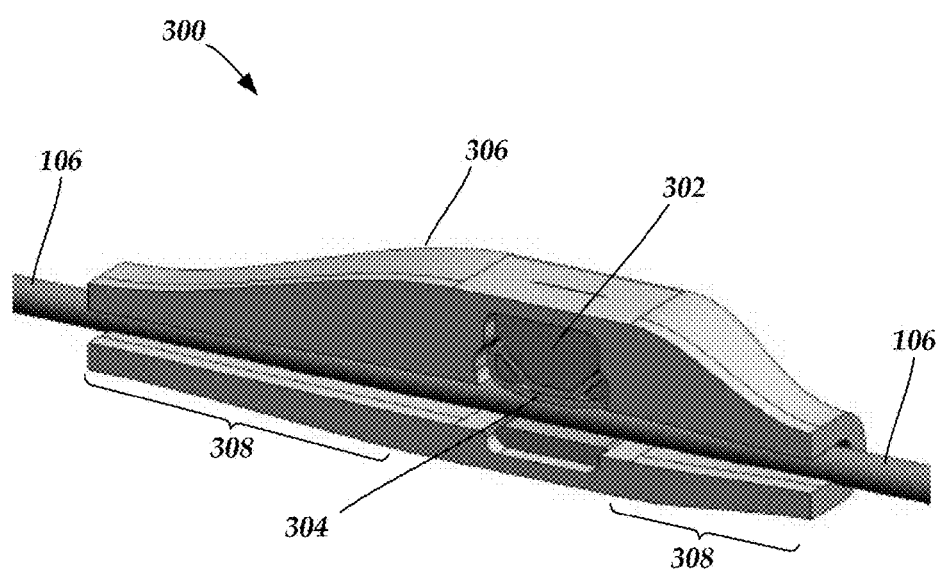
FIG. 3 is a schematic perspective view of a lead anchor for an electrical stimulation system according to an embodiment of the present invention.

FIG. 3 schematically illustrates a lead anchor 300 that permits a lead body 106 to be inserted into the lead anchor 300 without passing the proximal or distal ends of the lead though the lead anchor 300. The lead anchor 300 includes an anchor body 302, a flexible band 304, a fastener 308 (FIG. 4), and an exterior body 306. In at least some embodiments, the fastener 308, which may take the form of a set screw, can be actuated to urge or press the flexible band 304 into tight contact with the lead body 306, and thereby secure the lead body 106 within the anchor body 302 when sufficient torque has been applied to the fastener 308. For purposes of the detailed description herein, "sufficient torque" should be interpreted as providing enough torque to the fastener, and thus enough linear motion of the flexible band, to capture, secure or otherwise restrain the lead body 306 within the anchor body 302. FIG. 3 further illustrates that the lead anchor 300 includes end portions 308, which in turn will be described in more detail below with respect to FIG. 8.

The lead body 106 may be made from a non-conductive, biocompatible material such as, for example, silicone, polyurethane, polyetheretherketone ("PEEK"), epoxy, and the like or combinations thereof. The flexible band 304 may be made from the same material as the lead body or some other type of flexible, biocompatible, polymeric material.

Figure 4:
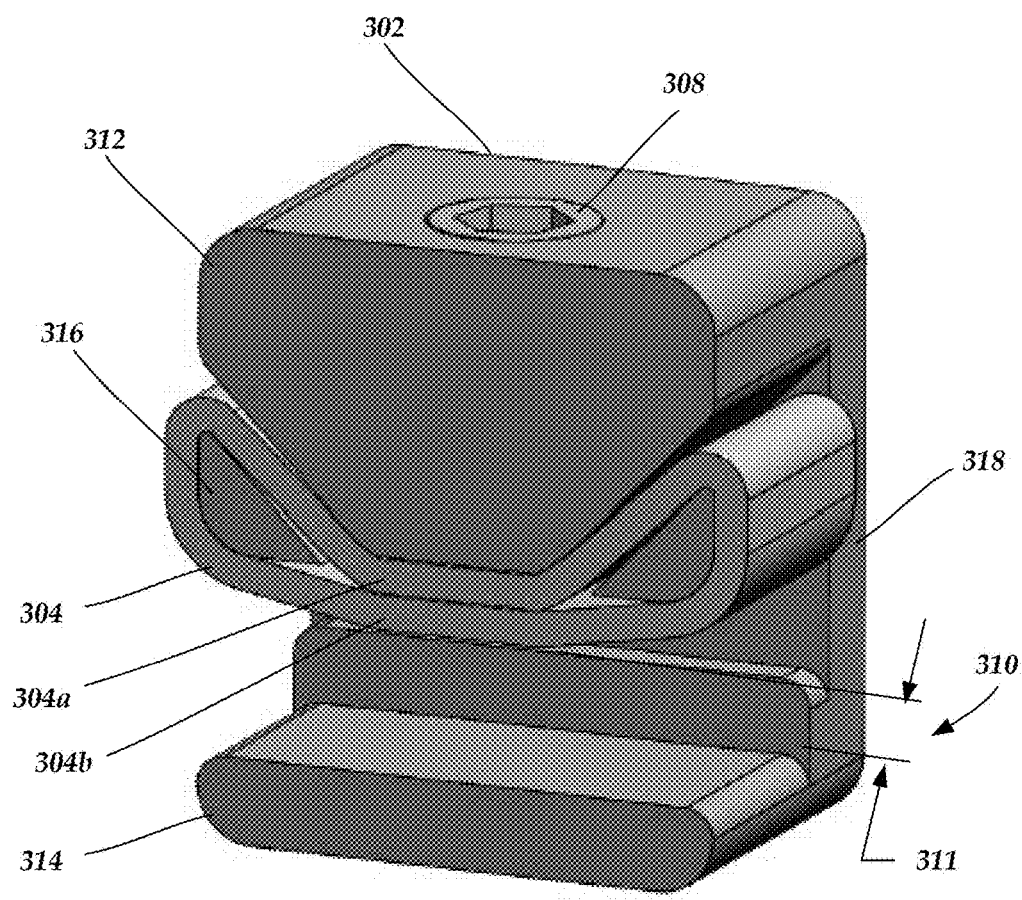
FIG. 4 is a schematic, perspective view of an anchor body and a flexible band of the lead anchor of FIG. 3 according to an embodiment of the present invention.

FIG. 4 shows the anchor body 302 and the flexible band 304 of the lead anchor 300 (FIG. 3). In at least some embodiments, the anchor body 302 takes the form of a unitary block, which may be machined or molded, having a band section 312, a support section 314, guide members 316, and a rigid wall 318 that fixedly couples the band section 312 to the support section 314. The band section 312 includes a threaded opening 313 (FIG. 5) for receiving the fastener 308. The guide members 316 extend from the rigid wall 318 and are configured to permit the flexible member 304 (taking the form of a continuous loop in the illustrated embodiment) to be slid over each of the guide members 316 such that two layers 304a, 304b of the flexible band member 304 are aligned for engagement by the fastener 308.

A first lead channel 310 is defined by the flexible band 302 and the support section 314 of the anchor body 302. The first lead channel 310 defines a gap or spaced-apart distance 311. In at least some embodiments, the first lead channel 310 includes an open side for receiving the lead body 106 (FIG. 3) and movement of the fastener 308 reduces the spaced-apart distance 311 as will be explained in further detail below.

Figure 5:
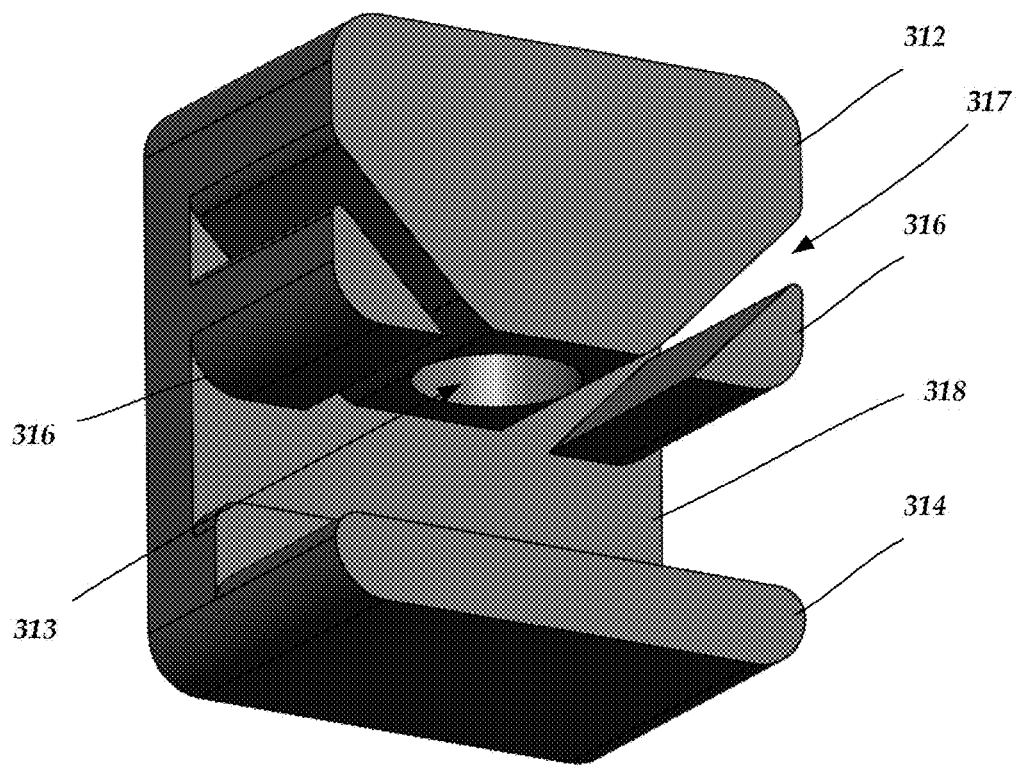
FIG. 5 is a schematic, perspective view of the anchor body FIG. 4 according to an embodiment of the present invention.

FIG. 5 illustrates the anchor body 302 according to at least some embodiments of the present invention. The guide members 316 cooperate with the band section 312 to form a band channel 317. Opposite ends of the continuous flexible band 302 (FIG. 4) are wrapped or disposed around the guide members 316. The guide members 316 may be integrally formed with the rigid wall 318 or otherwise attached to the rigid wall 318. In turn, the rigid wall 318 operates to maintain the band section 312 and the support section 314 at a fixed distance apart. The rigid wall 318 may be integrally formed with the band section 312 and the support section 314, or alternatively may be structurally attached by some other manner.

Figure 6A:
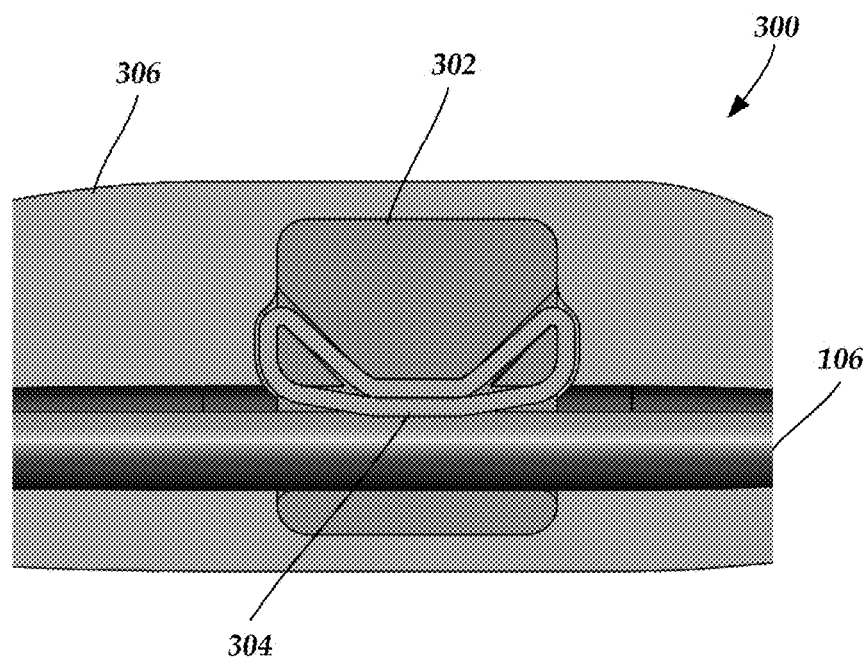
FIG. 6A is a side elevational view of the lead anchor of FIG. 3 in an OPEN position according to an embodiment of the present invention.
Figure 6B:
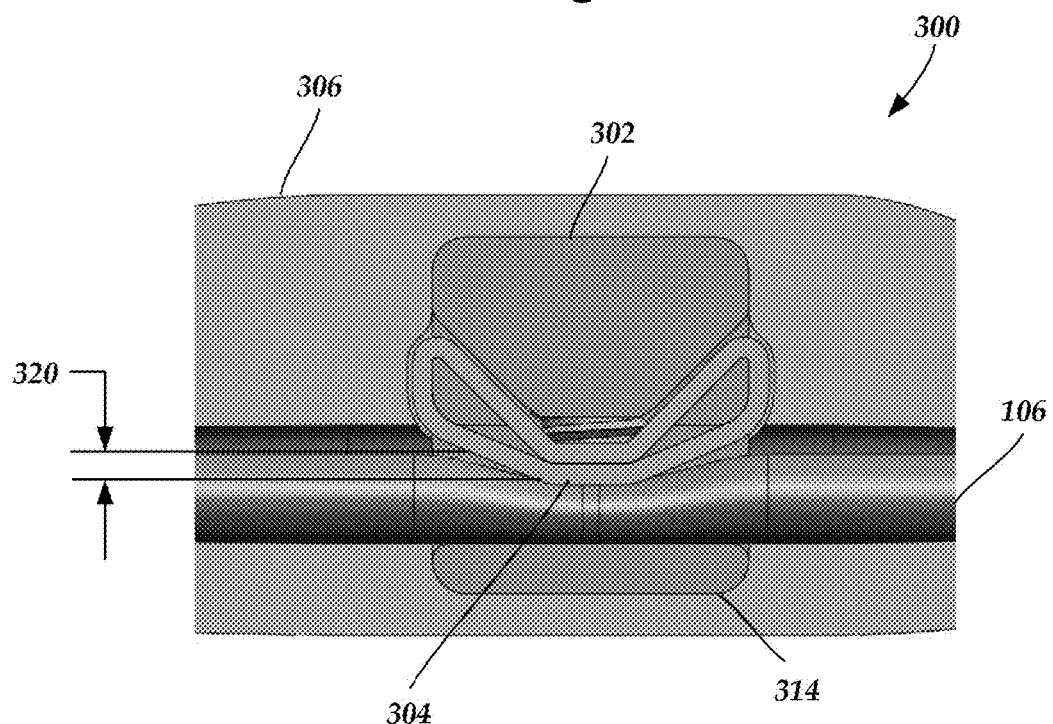
FIG. 6B is a side elevational view of the lead anchor of FIG. 3 in an CLOSED position according to an embodiment of the present invention.

FIGS. 6A and 6B show the lead anchor 300 in two different configurations. FIG. 5A shows the lead anchor 300 in an OPEN position that allows the lead body 106 to be laterally inserted (e.g., side loaded) into the anchor body 302 or laterally removed therefrom. In the OPEN position, the fastener 308 (FIG. 4) has been backed off to relieve pressure on the flexible band 304. Retracting the fastener 308 reduces a compressive force between the flexible band 302 and the lead body 106, which "opens" the lead anchor 300 for loading or releasing the lead body 106.

FIG. 6B, on the other hand, shows the lead anchor 300 in a CLOSED position in which the lead body 106 is captured, secured or otherwise restrained between the support section 314 and flexible band 304 due to pressure applied on the flexible band 302 by the fastener 308 (FIG. 4). Advancing the fastener 308 presses the flexible band 304 into physical contact with the lead body 106 or increases the physical contact. When the fastener 308 is sufficiently torqued, the compressive force between the flexible band 302 and the lead body 106 captures the lead body 106 within the first lead channel 310 (FIG. 4) of the lead anchor 300. In at least some embodiments, the torque generates a force that in turn generates a relative deflection 320. Additionally or alternatively, the deflection 320 may be the summation of at least some compressive deformation of the flexible band 302 and at least some compressive deformation of the lead body 106. In at least some embodiments, neither the flexible band 302 nor the lead body 106 are subjected to permanent (plastic) deformation or permanent damage when the fastener 308 is sufficiently torqued.

Figure 7A:
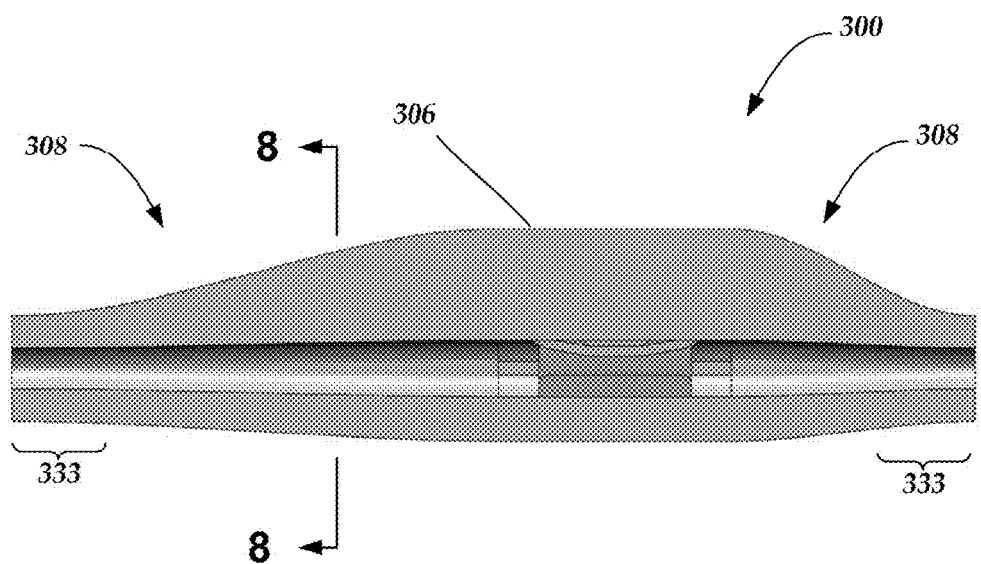
FIG. 7A is a side elevational view of an exterior body for a lead anchor according to an embodiment of the present invention.

FIG. 7A shows the lead anchor 300 having the exterior body 306 and the end portions 308. In at least some embodiments, the exterior body 306 may optionally vary in thickness with a greater thickness in a vicinity of the anchor body 302 and a tapered or reduced thickness near or at the end portions 308. Further, the exterior body 306 thickness may vary depending on a size or configuration of the lead anchor or on a destination within the patient. The exterior body 306 may be made from a flexible, polymeric material such as, but not limited to, a non-conductive, biocompatible material like silicone, polyurethane, polyetheretherketone ("PEEK"), epoxy, or combinations thereof. The exterior body 306 may be manufactured separate from the anchor body 302 and then placed over or molded onto the anchor body 302. In at least some embodiments, the end portions 308 are at the proximal and distal end portions of the exterior body 306. Although FIG. 7A shows the exterior body 306 as being non-symmetric with respect to the lead anchor 300, at least in some embodiments the exterior body 306 may be symmetric with respect to the lead anchor 300.

Figure 7B:
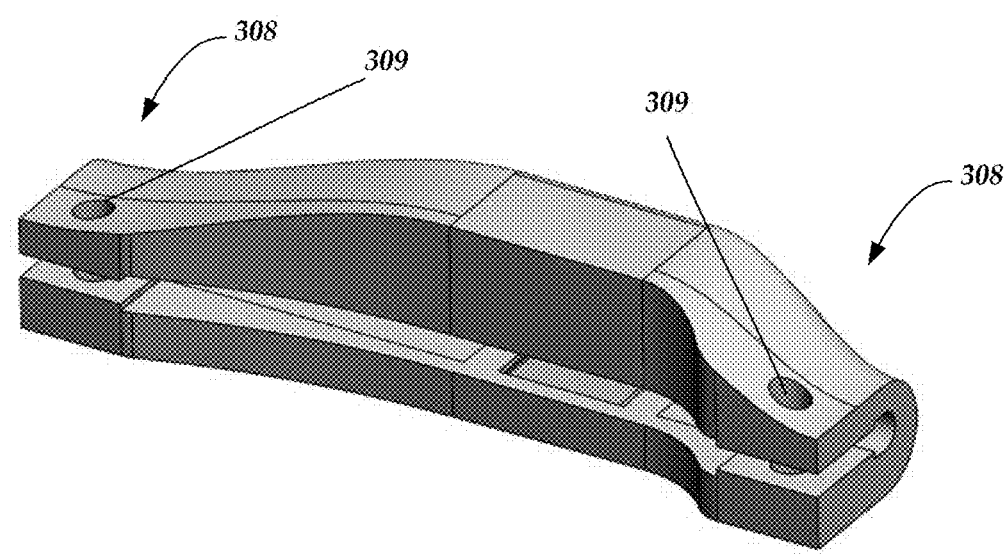
FIG. 7B is a schematic, perspective view of another exterior body having suture holes according to an embodiment of the present invention

FIG. 7B shows the end portions 308 having optional suture holes 309. In at least some embodiments, the suture holes 309 may provide an attachment point for sutures. Additionally or alternatively, the suture holes 309 hold the lead body within the end portions 308 to reduce or prevent migration of the lead body along or out of the lead channel.

In at least some embodiments, a suture (not shown) threaded through at least one of the suture holes 309 causes the respective end portion 308 to be narrowed or even pinched shut, thus capturing the lead body within the end portion 308 to reduce or prevent lead body migration.

Figure 8:
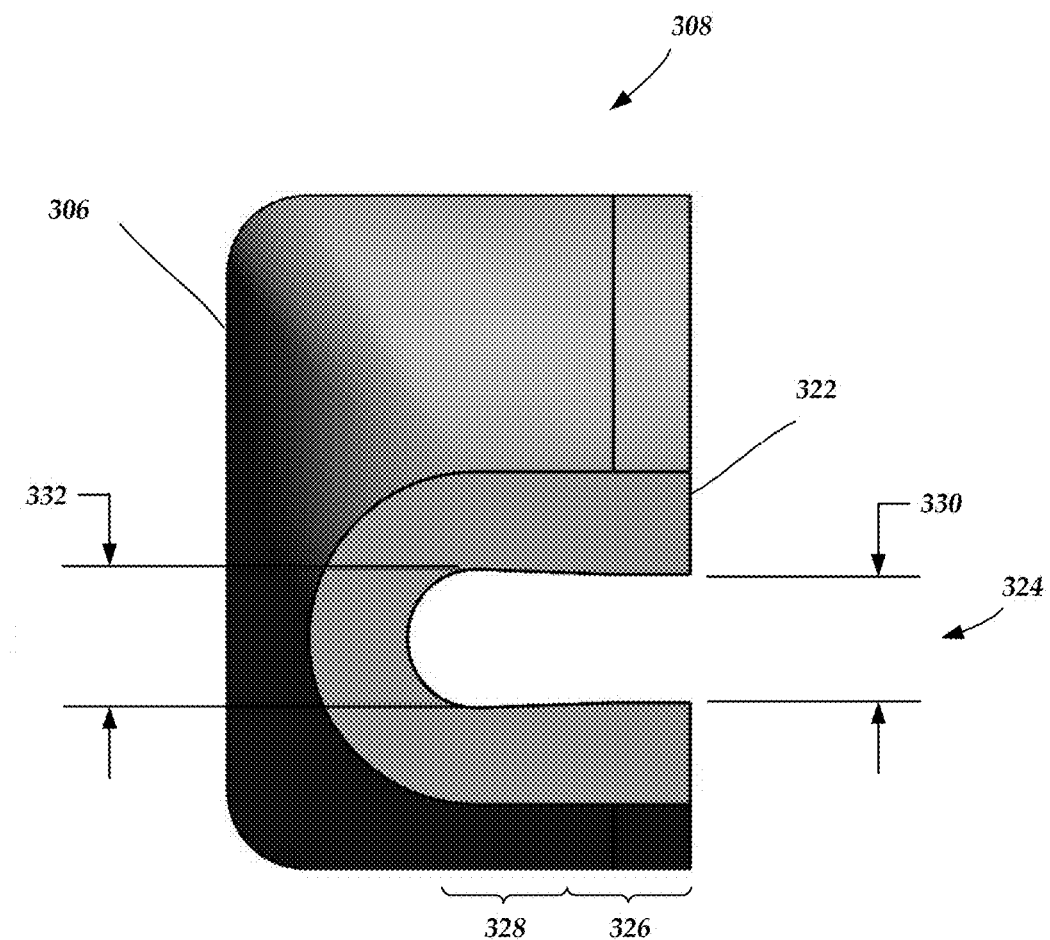
FIG. 8 is a cross-sectional view of an end portion of the exterior body of FIG. 7A taken along line 8-8 of FIG. 7A according to an embodiment of the present invention.

FIG. 8 shows one of the end portions 308 in which a section of the exterior body 306 forms a cuffed section 322 that defines a second lead channel 324 within the exterior body 306 and aligned with the first lead channel 310 (FIG. 4) within the anchor body 302 (FIG. 4). Additionally or alternatively, the first lead channel 310 and the second lead channel 324 cooperate to form a continuous lead channel. The second lead channel 324 includes an inlet region 326 and a retention region 328. The inlet region 326 defines an inlet gap 330 that is equal to or slightly less than the diameter of the intermediate portion of lead body to be received in the second lead channel 324. Thus, the lead body may need to be manipulated or urged through the inlet gap 330 during assembly. The retention region 328 defines a retention gap 332 that is larger, at least slightly larger, than the inlet gap 330 and at least equal to or larger than the diameter of the lead body. In at least some embodiments, the configuration of the end portion 308 described herein may be located only in far end sections 333 (FIG. 7A) of the exterior body 306.

Accordingly, the inlet gap 330 through which the lead body is inserted into the second lead channel 324 is narrower than the retention gap 332 where the lead body sits or rests when fully inserted into the exterior body 306. In at least some embodiments, this retaining aspect of the second lead channel 324 provides an amount of strain relief for the lead body or lead away from the lead anchor 300. And, at least in some embodiments, the larger retention gap 332 of the second lead body channel 324 allows the lead body to be retained within the exterior body 306 while minimizing unwanted compression or deformation of the lead body. In at least some embodiments, the far end portions of the exterior body 306 may also be sutured for retention of the lead body.

Figure 9:
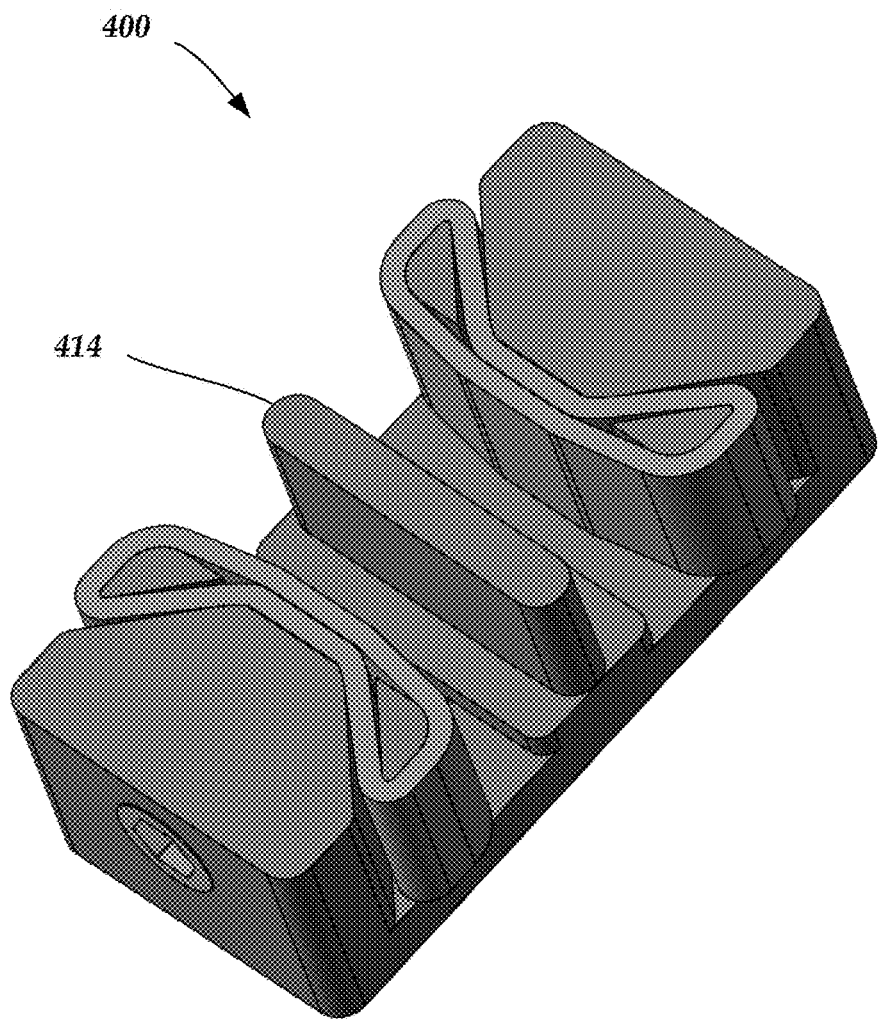
FIG. 9 is a schematic, perspective view of a dual lead anchor according to an embodiment of the present invention.

FIG. 9 shows a dual lead anchor body 400 configured to receive and anchor two lead bodies. The dual lead anchor body 400 includes two fasteners and two flexible bands. Each anchor body 400 may be opened or closed independent of the other. Optionally, an exterior body (not shown) may be overmolded or otherwise coupled to the dual lead anchor body 400.

Figure 10:
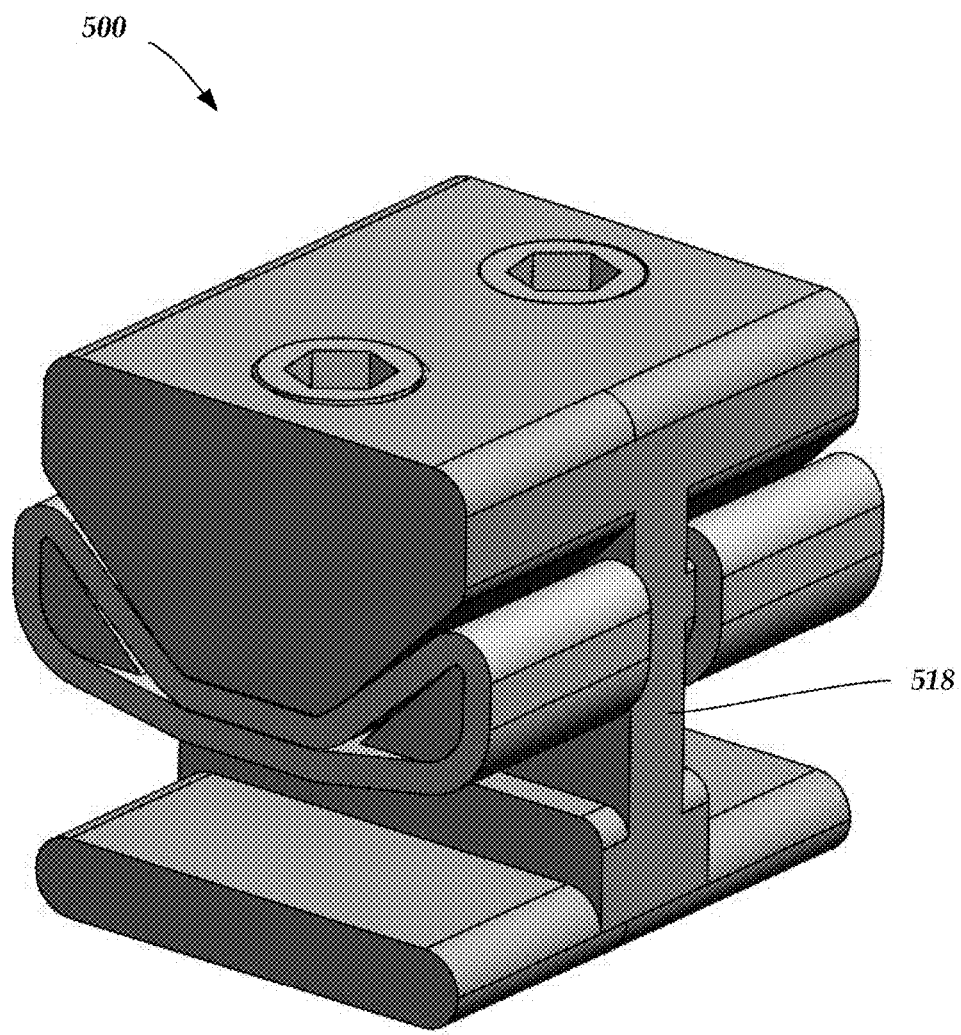
FIG. 10 is a schematic, perspective view of another dual lead anchor according to an embodiment of the present invention.

FIG. 10 shows another dual lead anchor body 500 configured to receive and anchor two lead bodies. The dual lead anchor body 500 includes two fasteners and two flexible bands. Each anchor body 500 may be opened or closed independent of the other. Optionally, an exterior body (not shown) may be overmolded or otherwise coupled to the dual lead anchor body 500.

The two embodiments of FIGS. 9 and 10 represent the basic lead anchor mirrored about a plane parallel to a support shelf 414 (FIG. 9) and about a plane perpendicular to a rigid wall 518 (FIG. 10).

Figure 11:
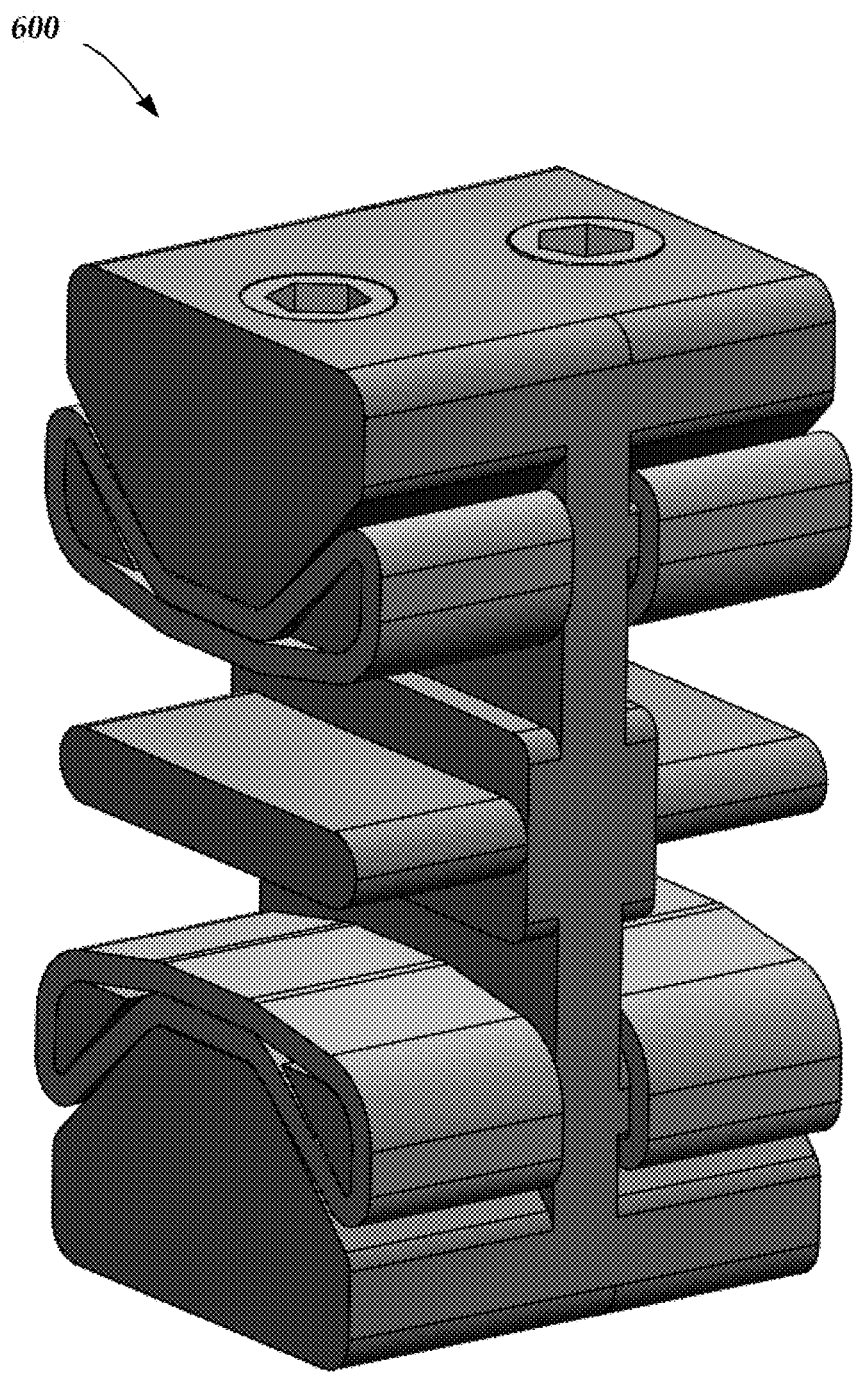
FIG. 11 is a schematic, perspective view of a quad lead anchor according to an embodiment of the present invention.

FIG. 11 shows a quad lead anchor body 600 configured to receive and anchor four lead bodies. The quad lead anchor body 600 includes four fasteners and four flexible bands. Each anchor body 600 may be opened or closed independent of any of the other anchor bodies. Optionally, an exterior body (not shown) may be overmolded or otherwise coupled to the quad lead anchor body 600.

Figure 12A:
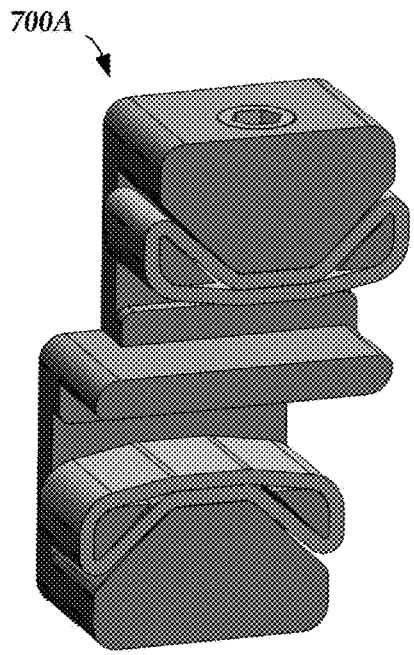
FIGS. 12A-12D are schematic, perspective views of various lead anchors according to different embodiments of the present invention.
Figure 12B:
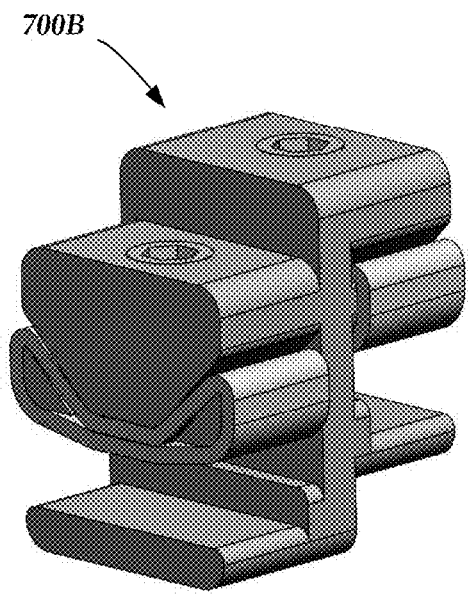
Figure 12C:
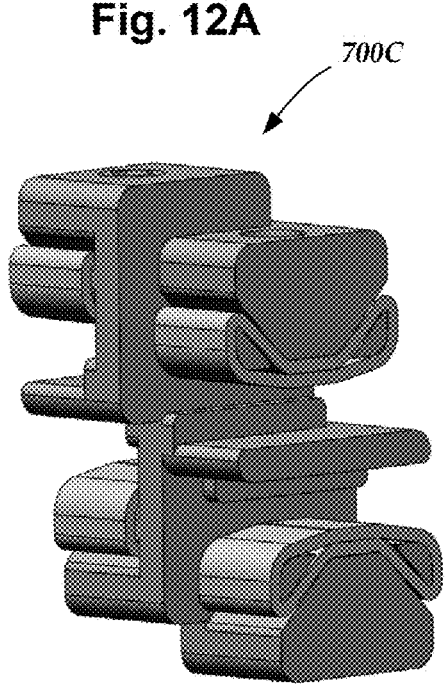
Figure 12D:
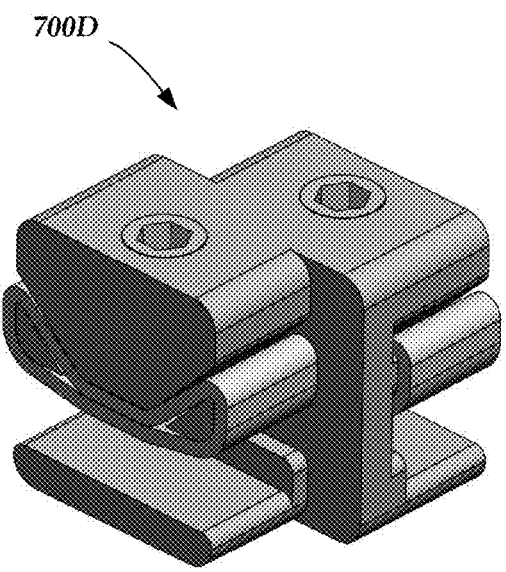

FIGS. 12A-12D show various exemplary lead anchors 700A-700D, respectively. The lead anchors may have lead anchor bodies that are offset, mirrored or otherwise configured in a variety of directions such as, but not limited to, vertically, horizontally, longitudinally, distally, proximally, laterally, etc. By way of example, the lead anchor bodies of lead anchor 700A in FIG. 12A are mirrored about a single support section and laterally offset relative to the support section. The lead anchor bodies of the lead anchor 700B in FIG. 12B are mirrored about a common wall and vertically offset relative to the common wall. The lead anchor bodies of the lead anchor 700C in FIG. 12C are offset laterally and vertically. The lead anchor bodies of the lead anchor 700D in FIG. 12D are mirrored about a common wall and horizontally offset relative to the common wall. It is appreciated that various anchor bodies may be adjoined in a variety of ways and that lead anchors 700A-700D are merely some possible, non-limiting examples. It is understood that the various directions used herein may depend upon a particular frame of reference for a particular application or in a particular environment. For example, the frame of reference for the directions used herein may, for example, be a piece of paper or a display screen.

Figure 13:
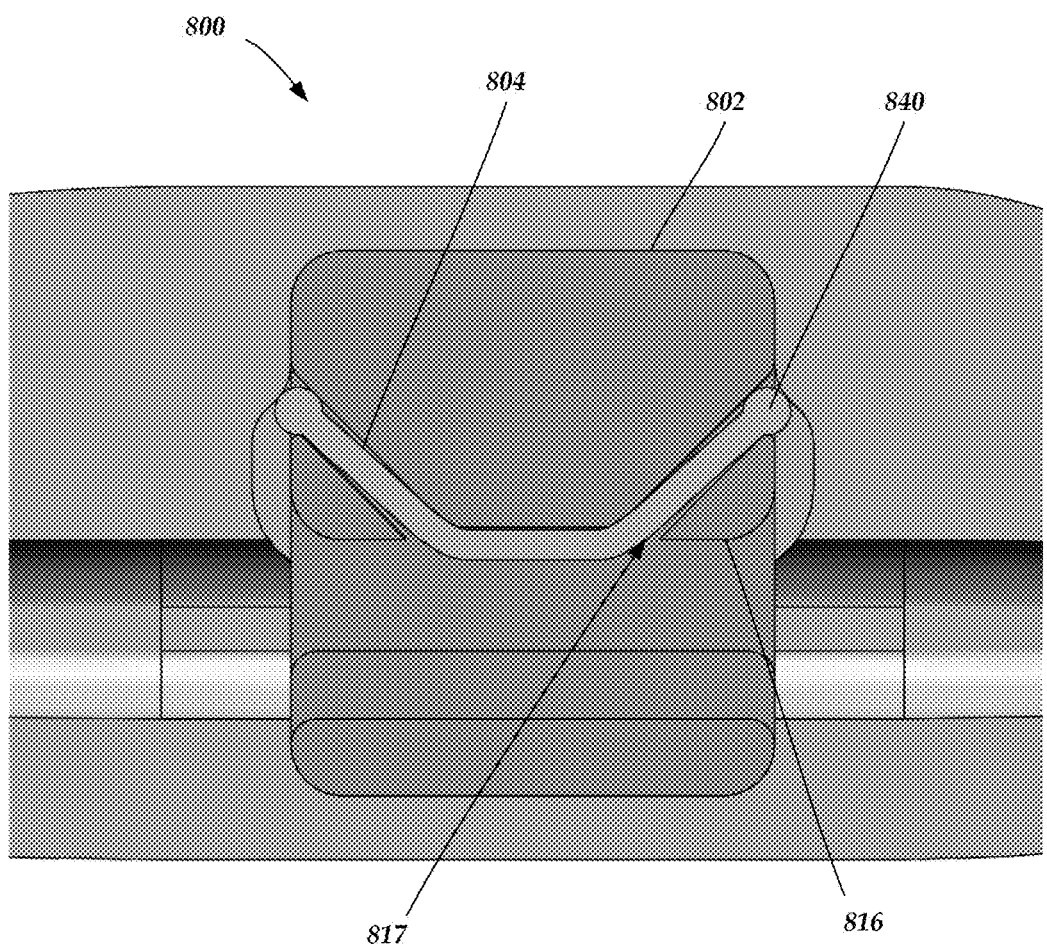
FIG. 13 is a side elevational view of a portion of a lead anchor having a non-continuous flexible band according to an embodiment of the present invention.

FIG. 13 shows another lead anchor 800 having a lead anchor body 802 and a non-continuous, flexible band 804. In the illustrated embodiment, the flexible band 804 includes bulbous end portions 840 that are thicker than the band thickness such that the bulbous end portions 840 cannot fit or slide through pathways 817 defined by guide members 816 of the lead anchor body 802.

Figure 14:
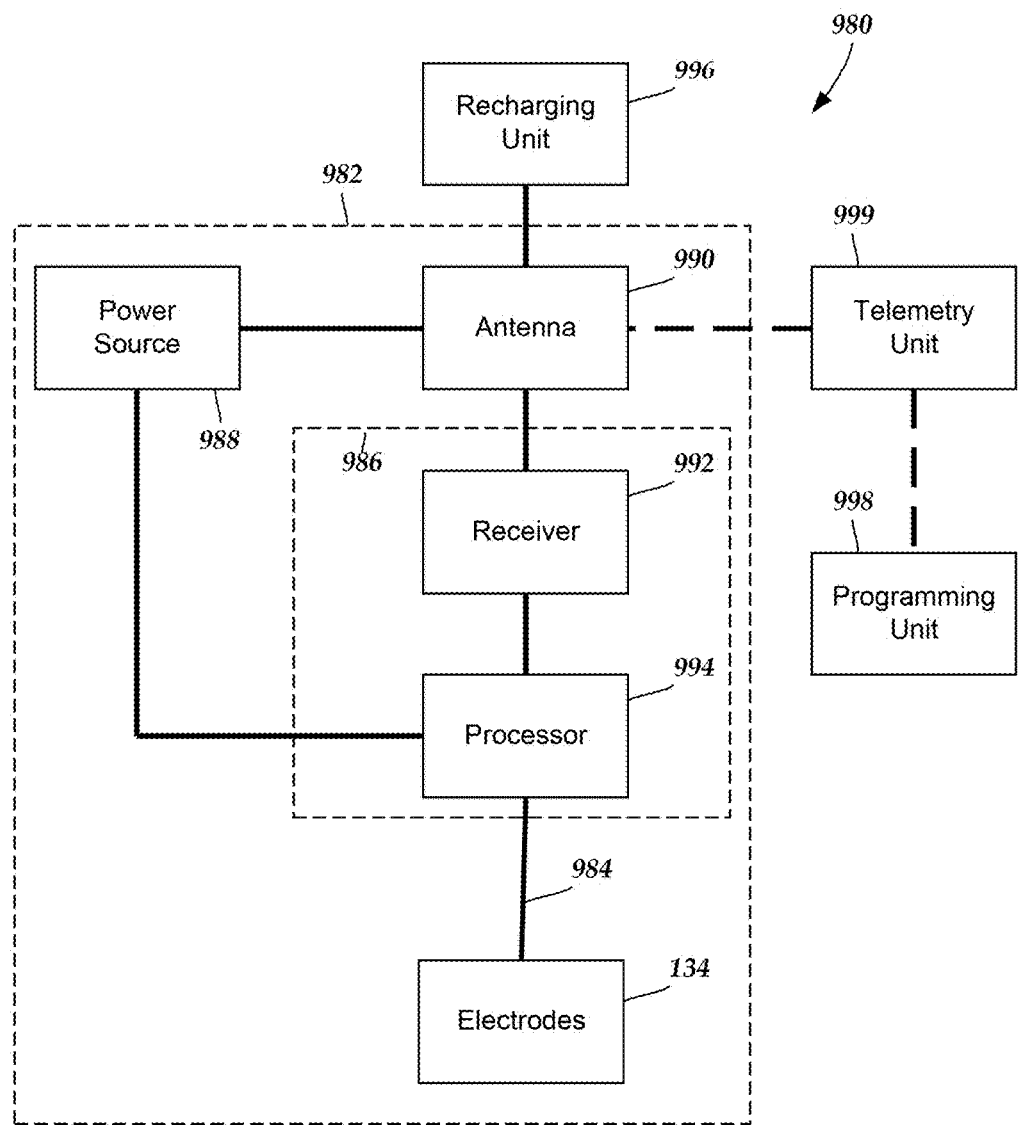
FIG. 14 is a schematic diagram of an electrical stimulation system according to an embodiment of the present invention.

FIG. 14 is a schematic overview of one embodiment of components of an electrical stimulation arrangement 980 that includes an electrical stimulation system 982 with a lead 984, stimulation circuitry 986, a power source 988, and an antenna 990. The electrical stimulation system can be, for example, any of the electrical stimulation systems described above. It will be understood that the electrical stimulation arrangement can include more, fewer, or different components and can have a variety of different configurations including those configurations disclosed in the stimulator references cited herein.

If the power source 988 is a rechargeable battery or chargeable capacitor, the power source may be recharged/charged using the antenna 990, if desired. Power can be provided for recharging/charging by inductively coupling the power source 988 through the antenna 990 to a recharging unit 996 external to the user. Examples of such arrangements can be found in the references identified above.

In one embodiment, electrical current is emitted by the electrodes (such as electrodes 134 in FIG. 1) on the lead 984 to stimulate nerve fibers, muscle fibers, or other body tissues near the electrical stimulation system. The stimulation circuitry 986 can include, among other components, a processor 994 and a receiver 992. The processor 994 is generally included to control the timing and electrical characteristics of the electrical stimulation system. For example, the processor 994 can, if desired, control one or more of the timing, frequency, strength, duration, and waveform of the pulses. In addition, the processor 994 can select which electrodes can be used to provide stimulation, if desired. In some embodiments, the processor 994 selects which electrode(s) are cathodes and which electrode(s) are anodes. In some embodiments, the processor 994 is used to identify which electrodes provide the most useful stimulation of the desired tissue.

Any processor can be used and can be as simple as an electronic device that, for example, produces pulses at a regular interval or the processor can be capable of receiving and interpreting instructions from an external programming unit 998 that, for example, allows modification of pulse characteristics. In the illustrated embodiment, the processor 994 is coupled to a receiver 992 which, in turn, is coupled to the antenna 990. This allows the processor 994 to receive instructions from an external source to, for example, direct the pulse characteristics and the selection of electrodes, if desired.

In one embodiment, the antenna 990 is capable of receiving signals (e.g., RF signals) from an external telemetry unit 999 that is programmed by the programming unit 998. The programming unit 998 can be external to, or part of, the telemetry unit 999. The telemetry unit 999 can be a device that is worn on the skin of the user or can be carried by the user and can have a form similar to a pager, cellular phone, or remote control, if desired. As another alternative, the telemetry unit 999 may not be worn or carried by the user but may only be available at a home station or at a clinician's office. The programming unit 998 can be any unit that can provide information to the telemetry unit 999 for transmission to the electrical stimulation system 982. The programming unit 998 can be part of the telemetry unit 999 or can provide signals or information to the telemetry unit 999 via a wireless or wired connection. One example of a suitable programming unit is a computer operated by the user or clinician to send signals to the telemetry unit 999.

The signals sent to the processor 994 via the antenna 990 and the receiver 992 can be used to modify or otherwise direct the operation of the electrical stimulation system 982. For example, the signals may be used to modify the pulses of the electrical stimulation system such as modifying one or more of pulse duration, pulse frequency, pulse waveform, and pulse strength. The signals may also direct the electrical stimulation system 982 to cease operation, to start operation, to start charging the battery, or to stop charging the battery.

Optionally, the electrical stimulation system 982 may include a transmitter (not shown) coupled to the processor 994 and the antenna 990 for transmitting signals back to the telemetry unit 999 or another unit capable of receiving the signals. For example, the electrical stimulation system 982 may transmit signals indicating whether the electrical stimulation system 982 is operating properly or not or indicating when the battery needs to be charged or the level of charge remaining in the battery. The processor 994 may also be capable of transmitting information about the pulse characteristics so that a user or clinician can determine or verify the characteristics.

The above specification provides a description of the structure, manufacture, and use of the invention. Since many embodiments of the invention can be made without departing from the spirit and scope of the invention, the invention also resides in the claims hereinafter appended.

What is claimed as new and desired to be protected by Letters Patent of the United States is:

1. A lead anchor comprising:
    an anchor body having a band section, guide members and a support section, the guide members and the support section spaced apart from each other in a fixed relationship, the band section and guide members defining a band channel;
    a flexible band coupleable to the guide members, wherein at least a portion of the flexible band is positionable within the band channel, wherein the flexible band and the support section define a first lead channel comprising a spaced-apart distance between the flexible band and the support section, and wherein the first lead channel includes an open side for allowing a lateral ingress or egress of a portion of a lead; and
    a fastener selectively movable relative to the anchor body to reduce or increase the spaced-apart distance of the first lead channel to hold or release, respectively, the portion of the lead within the first lead channel.

2. The lead anchor of claim 1, wherein the guide members are integrally formed with the anchor body.

3. The lead anchor of claim 1, wherein the flexible band forms a continuous loop.

4. The lead anchor of claim 3, wherein opposite ends of the loop are disposed around the guide members.

5. The lead anchor of claim 1, wherein the flexible band includes bulbous end portions that are larger than an opening of the band channel.

6. The lead anchor of claim 1, wherein the fastener is a set screw.

7. The lead anchor of claim 1, wherein the fastener directly engages with the flexible band.

8. The lead anchor of claim 1, wherein the anchor body includes a rigid wall extending between the band section and the support section to maintain the band section in the fixed relationship with the support section.

9. The lead anchor of claim 1, wherein reducing the spaced-apart distance of the first lead channel places the first lead channel in a closed position and increasing the spaced-apart distance of the first lead channel places the first lead channel in an open position.

10. The lead anchor of claim 1, further comprising an exterior body encapsulating at least a portion of the anchor body.

11. The lead anchor of claim 10, wherein a thickness of the exterior body varies along a longitudinal direction of the exterior body.

12. The lead anchor of claim 10, wherein the exterior body includes an end portion.

13. The lead anchor of claim 12, wherein the end portion defines a second lead channel having an open side to laterally receive another portion of the lead.

14. The lead anchor of claim 13, wherein the second lead channel includes a retention region that is larger than an inlet region.

15. An electrical stimulation system comprising:
    the lead anchor of claim 1;
    a control module having a housing and an electronic subassembly disposed in the housing; and
    a lead comprising:
        an array of electrodes selectively controllable by the control module; and
        a lead body carrying a plurality of conductors that are electrically coupled to the control module and electrically coupled to the array of electrodes, wherein a portion of the lead body is laterally insertable into or extractable from the first lead channel of the lead anchor.

16. The electrical stimulation system of claim 15, further comprising an exterior body encapsulating at least a portion of the anchor body.

17. The electrical stimulation system of claim 16, wherein the exterior body includes an end portion.

18. The electrical stimulation system of claim 17, wherein the end portion defines a second lead channel having an open side to laterally receive another portion of the lead body.

19. The electrical stimulation system of claim 18, wherein the second lead channel includes a retention region that is larger than an inlet region.

20. A method of assembling a lead with the lead anchor of claim 1, the method comprising:
    laterally inserting an intermediate portion of the lead through an open side of the first lead channel of the lead anchor; and
    reducing the spaced-apart distance of the first lead channel to capture the intermediate portion of the lead within the lead anchor.

* * * * *